United States Patent [19]

Scherowsky et al.

[11] Patent Number: 4,968,820
[45] Date of Patent: Nov. 6, 1990

[54] CHIRAL REACTION PRODUCTS PRODUCED FROM MESOGENIC MOLECULAR STRUCTURAL ELEMENTS AND BIFUNCTIONALLY REACTIVE BUTANETETRAOL DERIVATIVES, AND THEIR USE AS DOPANTS IN LIQUID CRYSTAL PHASES

[75] Inventors: Günter Scherowsky; Manel Gunaratne, both of Berlin, Fed. Rep. of Germany

[73] Assignee: Hoechst Aktiengesellschaft, Frankfurt am Main, Fed. Rep. of Germany

[21] Appl. No.: 220,377

[22] Filed: Jul. 11, 1988

Related U.S. Application Data

[63] Continuation of Ser. No. 14,465, Feb. 13, 1987, abandoned.

[30] Foreign Application Priority Data

Feb. 17, 1986 [DE] Fed. Rep. of Germany ....... 3604899

[51] Int. Cl.$^5$ ................. C07D 317/00; C07D 307/02; C07D 403/00; C07D 239/02
[52] U.S. Cl. .................................. 549/453; 549/476; 549/478; 544/295; 544/296; 544/298; 544/315; 558/399; 558/430; 560/1; 560/102; 560/112; 560/118
[58] Field of Search ................ 560/1, 102, 112, 118, 560/55, 59; 544/295, 296, 298, 315, 322, 330, 332, 336, 357; 549/20, 21, 22, 369, 371, 372, 451, 453, 476, 478; 252/299.63, 299.66, 299.01, 299.5, 299.61; 350/350 R, 350 S

[56] References Cited

U.S. PATENT DOCUMENTS 4,264,148 4/1981 Göbl-Wunsch et al. ....... 252/299 X
4,584,120 4/1986 Fujii et al. ...................... 560/118 X
4,650,600 3/1987 Heppke et al. ................. 252/299.01
4,673,529 6/1987 Sugimori et al. ............... 560/118 X
4,686,289 8/1987 Huynh-Ba et al. ............. 558/409 X

FOREIGN PATENT DOCUMENTS 0168043 1/1986 European Pat. Off. .

Primary Examiner—John W. Rollins
Attorney, Agent, or Firm—Curtis, Morris and Safford

[57] ABSTRACT

The new compounds produced from a molecular structural element with two chirality centers and at least one mesogenic structural element are defined by the general formula (I)

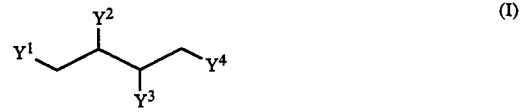

(I)

in which the symbols have the following meaning:
$Y^1$, $Y^2$, $Y^3$, $Y^4$ = in any two cases (a) hydroxy and MC—CO—O or, independently of each other, MC—CO—O and (b), independently of each other ($C_1$-$C_{10}$)alkoxy, MC denoting the molecular radical of a mesogenic carboxylic acid after splitting off a COOH group, and it being possible for $Y^2$ and $Y^3$, in the case of ($C_1$-$C_{10}$)alkoxy, also to be jointly part of a dioxolane ring, or $Y^1$ and $Y^4$ jointly = O as part of a tetrahydrofuran ring, and $Y^2$ and $Y^3$ = hydroxy and MC—CO—O or, independently of each other, MC—CO—O. Said esters preferably find application as dopants in twistable liquid crystal phases in which they produce temperature compensation and twisting.

9 Claims, 1 Drawing Sheet

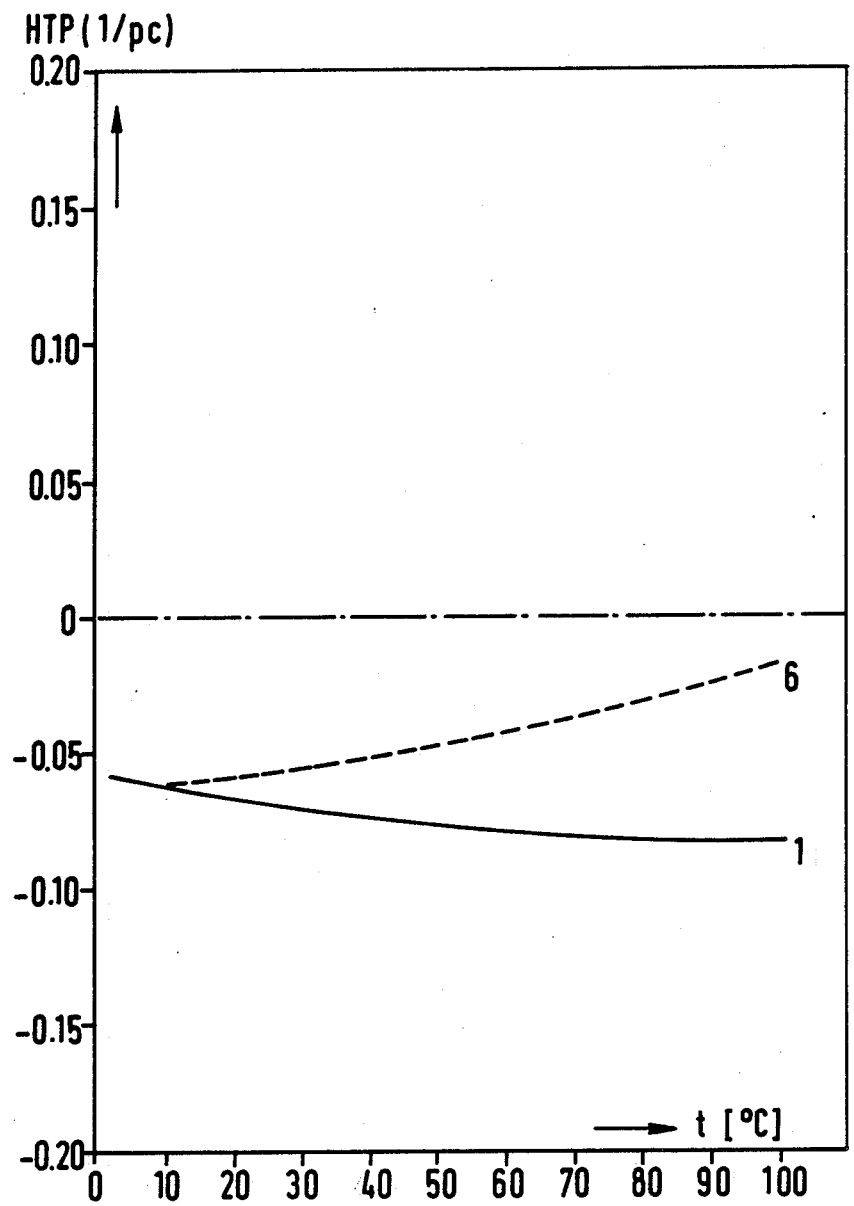

CHIRAL REACTION PRODUCTS PRODUCED FROM MESOGENIC MOLECULAR STRUCTURAL ELEMENTS AND BIFUNCTIONALLY REACTIVE BUTANETETRAOL DERIVATIVES, AND THEIR USE AS DOPANTS IN LIQUID CRYSTAL PHASES

This application is a continuation of application Ser. No. 07/014,465, filed Feb. 13, 1987, abandoned.

In general the characteristic curves of the electroptical effects used in liquid crystal displays vary with temperature. In particular, for a drive system employing multiplex operation, this results in difficulties which may lead to an undesirable restriction of the working temperature range. In the case of various electrooptical effects, the temperature dependence of the electrooptical characteristic curves can be advantageously influenced by addition of chiral compounds to the nematic liquid crystal via the temperature function of the pitch of the cholesteric helical structure thereby induced, as in the case of the cholesteric/nematic phase change effect, of the TN ("twisted nematic") cell and of the recently revealed SBE ("supertwisted birefringence effect"). The usual known dopants in general induce a pitch which increases with increasing temperature; dopants have also even been described recently which do not exhibit this often undesirable effect.

The addition of two different chiral dopants to nematic carrier substances is known from DE-C-No. 2,827,471 (=U.S. Pat. No. 4,264,148); in this case one chiral dopant produces a right-handed twist in the nematic carrier substance, while the other produces a left-handed twist. A decrease in the pitch is achieved by means of such a doping but to achieve this effect relatively high total concentrations are necessary which may have a negative effect on the other material parameters.

DE-A-No. 3,333,677 describes, inter alia, reaction products (esters) of chiral butane-2,3-diol with mesogenic carboxylic acids which may simplify the optimization of the temperature compensation in liquid crystal phases even as an individual addition. Said known esters often have twisting powers, however, which are still too low for certain applications.

The object of the present invention is therefore to discover new compounds which produce an optimization of the temperature compensation and also a considerable twisting of the liquid crystal phases even for relatively low added quantities when they are used, individually or as mixtures, as chiral dopants in liquid crystal phases; in addition, it should be possible, starting from a comparable basic structure, to alter the properties of the molecule in a certain direction by fairly small molecular variations.

The starting point of the invention is the known compounds comprising a molecular structural element with two chirality centers and at least one mesogenic molecular structural element. The novel compounds are defined by the general formula (I) of a butanetetraol derivative

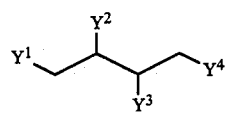

(I)

in which the symbols have the following meaning:

$Y^1$, $Y^2$, $Y^3$, $Y^4$=in any two cases (a) hydroxy and MC-CO-O or, independently of each other, MC—CO—O and (b), independently of each other, ($C_1$-$C_{10}$)alkoxy, MC denoting the molecular radical of a mesogenic carboxylic acid after splitting off a COOH group, and it being possible for $Y^2$ and $Y^3$, in the case of ($C_1$-$C_{10}$)alkoxy, also to be jointly a part of a dioxolane ring, or $Y^1$ and $Y^4$ jointly=O as part of a tetrahydrofuran ring and $Y^2$ and $Y^3$=hydroxy and MC—CO13 O or, independently of each other, MC-CO-O.

The said compounds are butane-1,2,3,4-tetraol derivatives singly or doubly esterified at the OH groups and doubly etherified, singly or doubly esterified 4,5-dihydroxy methyl-1,3-dioxolane derivatives or singly or doubly esterified 3,4-dihydroxytetrahydrofuran derivatives.

A further embodiment of the invention is a twistable liquid crystal phase containing at least one chiral compound, wherein the phase contains at least one compound of the general formula (I) as a chiral compound. The term "twistable liquid crystal phase" is to be understood to mean nematic, cholesteric, tilted smectic, in particular smectic C ($S_c$ or SmC), phases.

The novel twistable liquid crystal phases consist of 2 to 20, preferably 2 to 15 components, including at least one of the chiral dopants claimed according to the invention. The other constituents are preferably selected from the known compounds having nematic, cholesteric and/or tilted smectic phases, which include, for example, Schiff's bases, biphenyls, terphenyls, phenylcyclohexanes, cyclohexyl biphenyls, pyrimidines, cinnamic acid esters, cholesterol esters, and variously bridged, terminally polar polynuclear esters of p-alkylbenzoic acids. In general, the liquid crystal phases obtainable commercially already exist, before the addition of the chiral dopant, as mixtures of a wide variety of components, at least one of which is mesogenic i.e. a compound which, in the form of a derivative or mixed with certain associated components, exhibits a liquid crystal phase [=permits at least one enantiotropic (clearing point>melting point) or monotropic (clearing point<melting point) mesophase formation to be expected].

Using the newly developed compounds as dopant, it is possible to achieve a high twisting with a small quantity of dopant in liquid crystal phases, it being possible, in addition, for the compounds, individually or as a mixture, to have a pitch which is substantially independent of temperature change, i.e. the increase or decrease in the pitch is, in general, in the range from 1% to 1 o/oo per K. The novel compounds may further be used in thermotopography or for producing "blue phases" (=cholesteric systems with a relatively low pitch of e.g. less than 800 nm).

Of the compounds of the general formula (I) those are preferred in which the radical MC in MC—CO—O [expressed by the general formula (II)] has the following meaning:

in which the symbols have the following meanings:

R=a straight-chain or branched ($C_1$-$C_{12}$)alkyl, it being possible for one or two non-adjacent $CH_2$ groups to be replaced by O atoms, or if n1=1, also F, Cl, Br or CN, A¹, A²=, independently of each other, 1,4-phenylene, diazine-2,5-diyl, diazine-3,6-diyl, 1,4-cyclohexylene, 1,3-dioxane-2,5-diyl, 1,3-dithiane-2,5-diyl or 1,4-bicyclo[2.2.2]octylene, it being possible for these groups also to be at least singly substituted by F, Cl, Br, CN and/or (C₁-C₁₂)alkyl (one or two non-adjacent CH₂ groups are optionally replaced by O atoms), B=CO—O, O—CO, CH₂—CH₂, OCH₂, CH₂O, CH=N, N=CH, N=N, N(O)=N, and n1, n2, n3=independently of each other, 0, 1 or 2, n1 and n3 not being 0 at the same time.

Of these compounds those are in turn preferred in which the symbols have the following meaning: R=straight-chain (C₄-C₁₀)alkyl it being possible for a CH₂ group to be replaced by an O atom, A¹, A²=independently of each other, unsubstituted 1,4-phenylene, 1,4-cyclohexylene or diazine-2,5-diyl, B=CO—O or O—CO, n1=1, n2=0 or 1, and n3=1 or 2.

In addition, in the general formula (I), the compounds are preferred in which the symbols have the following meaning: (a) Y¹=Y⁴=MC—CO—O or Y¹=hydroxy and Y⁴=MC—CO—O and Y²=Y³=(C₁-C₅)alkoxy or, in the 1,3-dioxolane ring, jointly the ring positions 1 to 3 with C₁-C₅ in position 2, (b) Y²=Y³=MC—CO—O or Y²=OH and Y³=MC—CO—O and Y¹ and Y⁴ jointly O as part of a tetrahydrofuran ring.

The liquid crystal phases contain in general 0.01 to 70% by weight, in particular 0.05 to 50% by weight, of the novel dopant or dopants.

EXAMPLES

General working procedure for preparing compounds 1 to 5.

10 to 40 mg of dimethylaminopyridine and 1.5 mmol of the mesogenic carboxylic acid are added to 1 mmol of the (R,R)-(+)-2,3-dimethoxy-1,4-butanediol in 10 to 50 ml of anhydrous methylene chloride or dimethylformamide while stirring. At a temperature of 0° C., 1.5 mmol of dicyclohexylcarbodiimide are added and stirring is carried out for 10 minutes at this temperature and then for 20 h at room temperature. Precipitated urea is filtered off, the filtrate is evaporated down in vacuum and the residue left is taken up in methylene chloride. After any filtration necessary, the organic solvent is distilled off and the residue chromatographed on silica gel. The following compounds whose structures have been established by spectroscopic data and elementary analysis, are prepared by this procedure [see also D. Seebach, Helv. Chim Acta 60, 301 (1977)]:

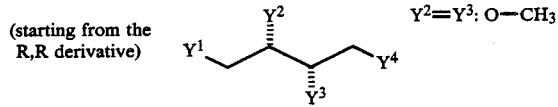

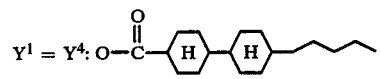

(1)

(R,R)-2,3-dimethoxy-1,4-bis-(4'-trans-n-pentyl-4-trans-dicyclohexylcarbonyloxy)butane

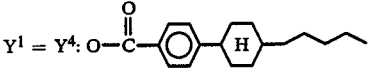

(2)

(R,R)-2,3-dimethoxy-1,4-bis[4-(trans-4-n-pentyl-cyclohexyl)benzoyloxy]butane

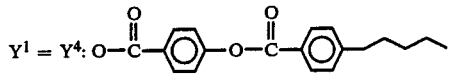

(3)

(R,R)-2,3-dimethoxy-1,4-bis[4-(4-n-hexyloxybenzoyloxy) benzoyloxy]butane

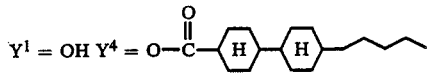

(4)

(R,R)-1-hydroxy-2,3-dimethoxy-4-(4'-trans-n-pentyl-4-trans-dicyclohexylcarbonyloxy)butane

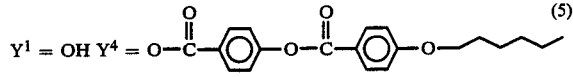

(5)

(R,R)-1-hydroxy-2,3-dimethoxy-4-[4-(4-n-hexyloxybenzoyloxy)benzoyloxy]butane

PREPARATION OF COMPOUNDS 6 to 8

The procedure is in accordance with the above general working procedure, but starting from (R,R)-(+)-2,2-dimethyl-4,5-bis(hydroxymethyl)-1,3-dioxolane [see A. Halay Coll. Czech. Chem. Commun. 47, 173 (1982)].

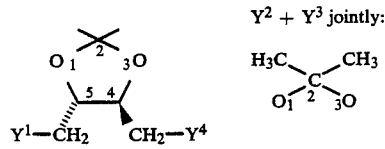

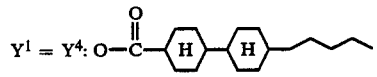

(6)

(R,R)-2,2-dimethyl-4,5-bis(4'-trans-n-pentyl-4-trans-dicyclohexylcarbonyloxymethyl)-1,3-dioxolane

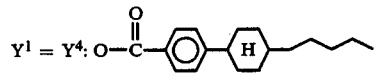

(7)

(R,R)-(—)-2,2-dimethyl-4,5-bis[4-(trans-4-n-pentylcyclohexyl)benzoyloxymethyl]-1,3-dioxolane

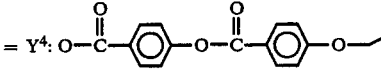

(8)

R,R-(—)2,2-dimethyl-4,5-bis[4-(4-n-hexyloxy-benzoyloxy) benzoyloxymethyl]-1,3-dioxolane

PREPARATION OF COMPOUNDS 9 and 10

The procedure is in accordance with the above general working procedure, but starting from (R,R)-(+)-3,4-dihydroxytetrahydrofuran [see F. C. Hartman and R. Barker, J. Org. Chem. 28, 1004 (1963)].

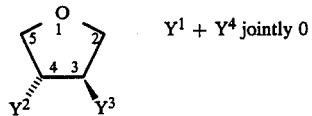

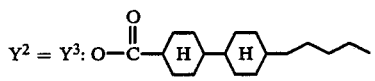 (9)

(R,R)-3,4-bis(4'-trans-n-pentyl-4-trans-dicyclohexylcarbonyloxy)tetrahydrofuran

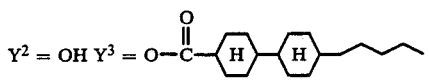 (10)

R,R-4-hydroxy-3-(4'-trans-n-pentyl-4-trans-dicyclohexylcarbonyloxy)tetrahydrofuran

TABLE

| Compound No. | Temperature range (°C.) of the twisting power measurement | Twisting power p.c (μm. % by weight) | Melting point (°C.) |
|---|---|---|---|
| 1 | 10–100 | −16 → −12 | 103–111 |
| 2 | 10–100 | −12 → −9 | 109–110 |
| 3 | 10–100 | −13 → −10.5 | 118–119 |
| 4 | — | — | 192–194 |
| 5 | — | — | 56–58 |
| 6 | 10–100 | −16 → −47 | 94–96 |
| 7 | — | — | 148–150 |
| 8 | — | — | — |
| 9 | — | — | 185–187 |
| 10 | — | — | 234 |

The measurement of the twisting power is carried out in a commercially available nematic wide-range mixture ("RO-TN 404" manufactured by the Hoffmann-La Roche Aktiengesellschaft (Basel/Switzerland)) with a clearing point of 104° C.

In the accompanying drawing the HTP values are plotted as a function of the temperature for some of the novel compounds. —HTP ("helical twisting power")=1/p.c (p=pitch of the induced helical structure in μm, c=concentration of the chiral dopant in % by weight).

If the shape of the curve of the HTP values of the compounds 1 and 6 in the drawing are compared with each other, it is evident that the R,R-derivative 1 induces a left-handed helix with HTP rising as temperature increases, but if the substituents $Y^2$ and $Y^3$ are linked to form a part of a dioxolane ring, the HTP falls as the temperature increases.

We claim:

1. A compound containing a molecular structural element with two chirality centers and at least one mesogenic molecular structural element, which compound has the formula (I)

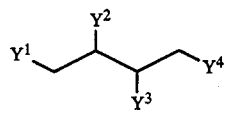 (I)

wherein:
two of $Y^1$, $Y^2$, $Y^3$ and $Y^4$ are hydroxy and MC—CO—O, or independently of each other MC—CO—O and the other two of $Y^1$, $Y^2$, $Y^3$ and $Y^4$ are independently of each other ($C_1$–$C_{10}$)alkoxy, wherein MC is a mesogenic group of the formula (II)

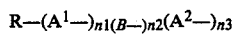 (II)

wherein:
R is a straight-chain or branched ($C_1$–$C_{12}$)alkyl group, in which one $CH_2$ group may be replaced by an O atom,
$A^1$, $A^2$ are independently of each other 1,4-phenylene, diazine-2,5-diyl, diazine-3,6-diyl, or 1,4-cyclohexylene, with the proviso that $A^1$ and $A^2$ are not both heterocyclic at the same time,
B is CO—O, O—CO, $CH_2$—$CH_2$, $OCH_2$ or $CH_2O$, and
n1, n2, n3 are independently of each other 0 or 1, n1 and n3 not being 0 at the same time.

2. A twistable liquid crystal mixture containing at least two components, wherein at least one component is a chiral compound of the formula (I) as claimed in claim 1.

3. A liquid crystal mixture as claimed in claim 2 wherein the chiral compound of the formula (I) is present in an amount of from 0.01 to 70% by weight.

4. A compound containing a molecular structural element with two chirality centers and at least one mesogenic molecular structural element, which compound has the formula (I)

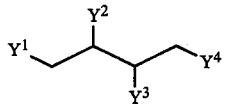 (I)

wherein
$Y^1$ and $Y^4$ are hydroxy and MC—CO—O, or independently of each other MC—CO—O and $Y^2$ and $Y^3$ together form a dioxolane ring, or $Y^1$ and $Y^4$ jointly are O and form a tetrahydrofuran ring, and $Y^2$ and $Y^3$ are hydroxy and MC—CO—O or, independently of each other, MC—CO—O, wherein MC is a mesogenic group of the formula (II)

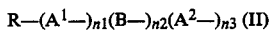 (II)

wherein:
R is a straight-chain or branched ($C_1$–$C_{12}$)alkyl group, in which one $CH_2$ group may be replaced by an O atom,
$A^1$, $A^2$ are independently of each other 1,4-phenylene, diazine-2,5-diyl, diazine-3,6-diyl, or 1,4-cyclohexylene, with the proviso that $A^1$ and $A^2$ are not both heterocyclic at the same time,
B is CO—O, O—CO, $CH_2$—$CH_2$, $OCH_2$ or $CH_2O$, and n1, n2, n3 are independently of each other 0 or 1 n1 and n3 not being 0 at the same time.

5. A twistable liquid crystal mixture containing at least two components, wherein at least one component is a chiral compound of the formula (I) as claimed in claim 4.

6. A liquid crystal mixture as claimed in claim 5 wherein the chiral compound of the formula (I) is present in an amount of from 0.01 to 70% by weight.

7. A compound containing a molecular structural element with two chirality centers and at least one mesogenic molecular structural element, which compound has the formula (I)

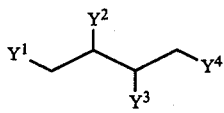
(I)

wherein:

$Y^1$ and $Y^4$ are independently of each other MC—CO—O and $Y^2$ and $Y^3$ are independently of each other $(C_1-C_{10})$alkoxy, wherein MC is a mesogenic group of the formula (II)

$$R-(A^1-)_{n1}(B-)_{n2}(A^2-)_{n3} \qquad (II)$$

wherein:

R is a straight-chain or branched $(C_1-C_{12})$alkyl group, in which one $CH_2$ group may be replaced by an O atom, $A^1$, $A^2$ are independently of each other 1,4-phenylene, diazine-2,5-diyl, diazine-3,6-diyl, or 1,4-cyclohexylene, with the proviso that $A^1$ and $A^2$ are not both heterocyclic at the same time, B is CO—O, O—CO, $CH_2$—$CH_2$, $OCH_2$ or $CH_2O$, and n1, n2, n3 are independently of each other 0 or 1 n1 and n3 not being 0 at the same time.

8. A twistable liquid crystal mixture containing at least two components, wherein at least one component is a chiral compound of the formula (I) as claimed in claim 7.

9. A liquid crystal mixture as claimed in claim 8 wherein the chiral compound of the formula (I) is present in an amount of from 0.01 to 70% by weight.

* * * * *